(12) United States Patent
Risch

(10) Patent No.: US 11,039,902 B2
(45) Date of Patent: Jun. 22, 2021

(54) MARKER ELEMENT AND METHOD FOR THE PRODUCTION THEREOF

(71) Applicant: BIOTRONIK AG, Buelach (CH)

(72) Inventor: Fabian Risch, Schaffhausen (CH)

(73) Assignee: Biotronik AG, Buelach (CH)

( * ) Notice: Subject to any disclaimer, the term of this patent is extended or adjusted under 35 U.S.C. 154(b) by 0 days.

(21) Appl. No.: 16/390,719

(22) Filed: Apr. 22, 2019

(65) Prior Publication Data
US 2019/0321128 A1    Oct. 24, 2019

(30) Foreign Application Priority Data
Apr. 24, 2018 (EP) .................................... 18168896

(51) Int. Cl.
*A61B 90/00*    (2016.01)
*A61F 2/00*    (2006.01)
*A61F 2/90*    (2013.01)

(52) U.S. Cl.
CPC ................ *A61B 90/39* (2016.02); *A61F 2/90* (2013.01); *A61B 2090/3966* (2016.02); *A61F 2220/005* (2013.01); *A61F 2240/001* (2013.01); *A61F 2250/0098* (2013.01); *Y10T 156/1062* (2015.01)

(58) Field of Classification Search
None
See application file for complete search history.

(56) References Cited

U.S. PATENT DOCUMENTS

| 2006/0235505 A1 | 10/2006 | Oepen et al. |
| 2011/0319982 A1 | 12/2011 | Bayer et al. |
| 2017/0119555 A1 | 5/2017 | Bayer |

FOREIGN PATENT DOCUMENTS

| EP | 1570808 A1 | 9/2005 |
| EP | 2399619 A2 | 12/2011 |
| EP | 2526901 A1 | 11/2012 |
| EP | 3165238 A1 | 5/2017 |
| EP | 3281648 A1 | 2/2018 |
| EP | 3348239 A1 | 7/2018 |
| WO | 2007105067 A1 | 9/2007 |
| WO | 2016201317 A1 | 12/2016 |

OTHER PUBLICATIONS

European Patent Office Search Report of EP 18168896.1, dated Nov. 13, 2018.

*Primary Examiner* — Linda L Gray
(74) *Attorney, Agent, or Firm* — Laurence A. Greenberg; Werner H. Stemer; Ralph E. Locher

(57) ABSTRACT

A method produces a marker element, which is composed of two radiopaque layers and an interposed adhesive layer. The marker element is heated and joined into the eyelet of a stent. The introduction of the mechanical force causes the two layers of the marker element to be compressed, whereby the available volume is reduced for the softened adhesive of the adhesive layer. Consequently, the softened adhesive from the adhesive layer is pushed out of the side of the marker element, so that the adhesive flows into the empty volume of the adhesive gap between the marker element and the inner edge of the eyelet of the scaffold and bonds to the inner edge of the eyelet.

12 Claims, 11 Drawing Sheets

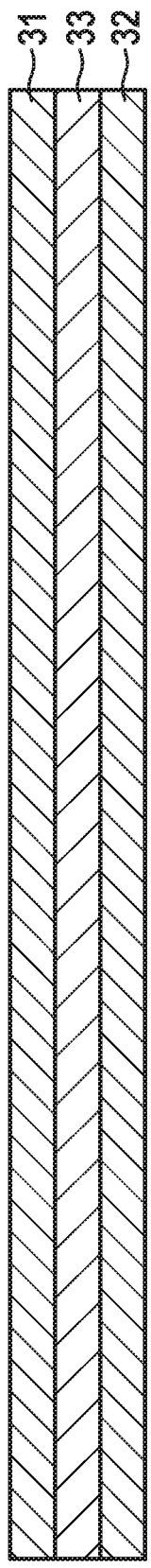
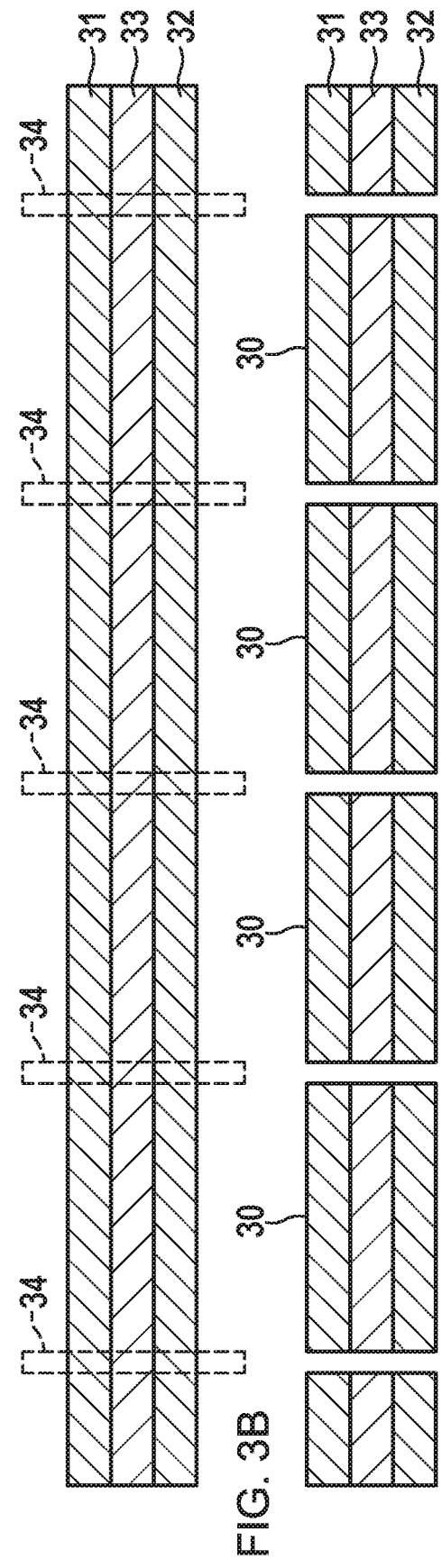
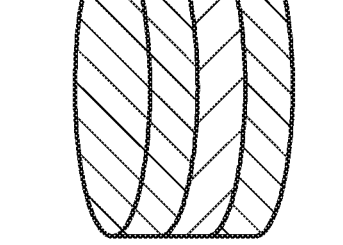
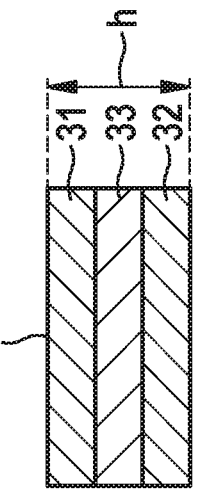
FIG. 3A  FIG. 3B  FIG. 3C  FIG. 3D  FIG. 3E

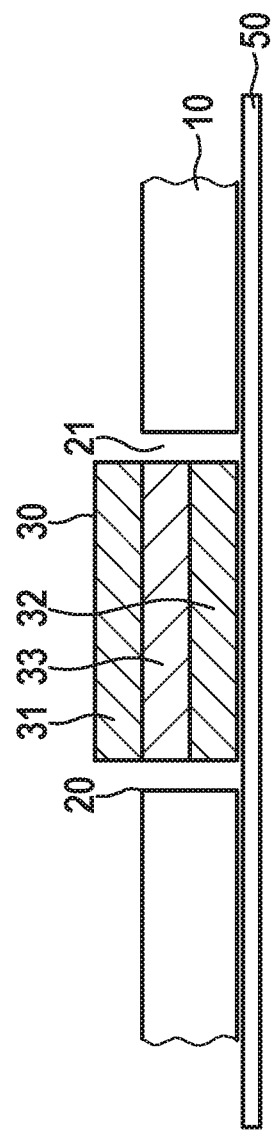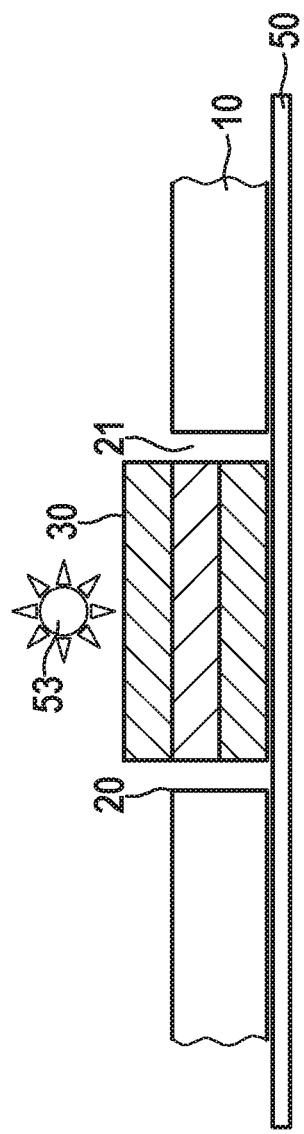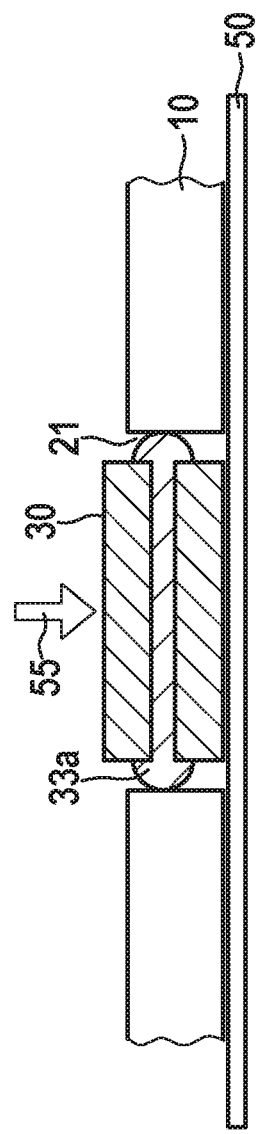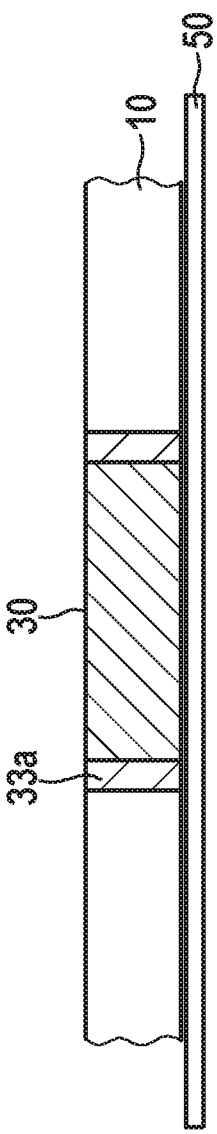

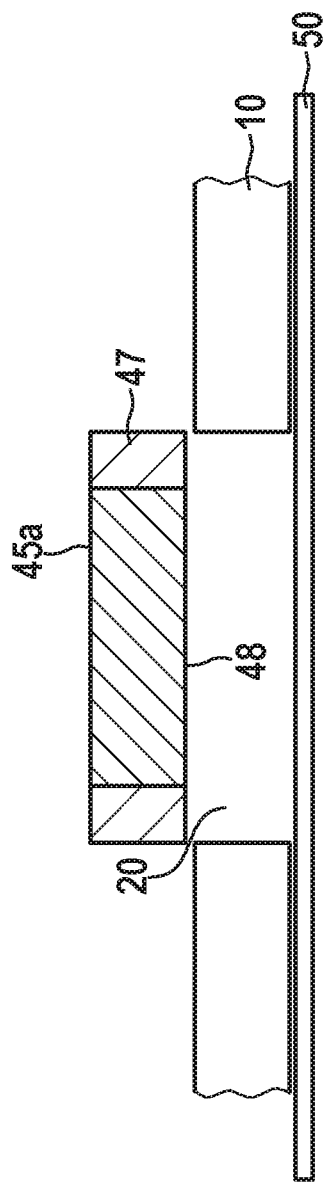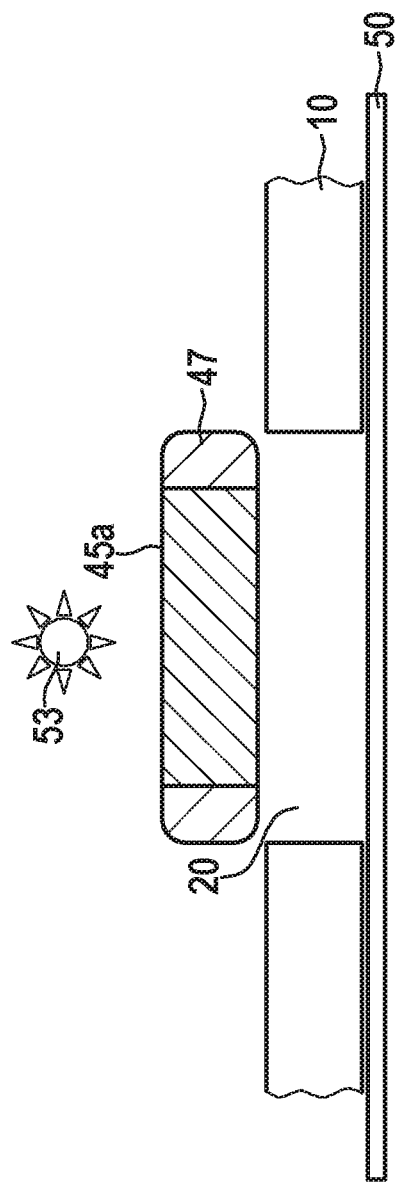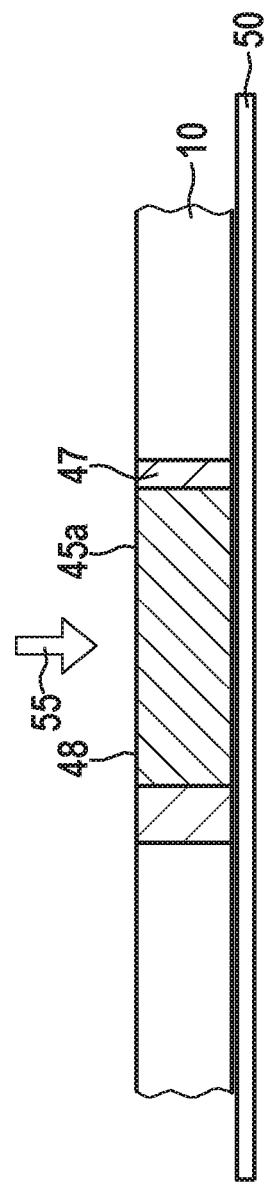

MARKER ELEMENT AND METHOD FOR THE PRODUCTION THEREOF

CROSS-REFERENCE TO RELATED APPLICATION

This application claims the priority, under 35 U.S.C. § 119, of European application EP 18 168 896.1, filed Apr. 24, 2018; the prior application is herewith incorporated by reference in its entirety.

BACKGROUND OF THE INVENTION

Field of the Invention

The present invention relates to a marker element for an implant, to a scaffold for an implant comprising a marker element, and to a method for producing such a marker element and such a scaffold.

The present invention moreover relates to an implant, and in particular to an intraluminal endoprosthesis, comprising a scaffold and a marker element that is attached to the scaffold and comprises, at least in a portion of the volume thereof, a material composition different from the material of the scaffold, which preferably comprises radiopaque and/or X-ray opaque material, and to a method for producing such an implant.

The implants are endovascular prostheses (endoprostheses, stents) or other implants that can be used to treat stenoses (vascular constrictions). These usually comprise a scaffold in the form of a hollow cylindrical or tubular base mesh, which is open at the two longitudinal ends of the tubes. Such a scaffold usually comprises a plurality of mutually connected struts, which form the base mesh. The tubular base mesh of such an endoprosthesis is inserted into the vessel requiring treatment and is intended to support the vessel. Other scaffold forms are likewise possible. The present invention further relates to implants that can be used in the field of orthopedics, for example for the skull area, and in particular to implants that, due to the small size and wall thickness thereof, have low X-ray visibility. The invention can likewise be used for stents in the neurovascular field. The important factor here is to keep the blood vessels supplying the brain open with absorbable Mg stents. These systems are used to prevent acute ischemic strokes.

Stents or other implants frequently comprise metallic materials in the scaffold thereof. The metallic materials can form a biodegradable substance, wherein polymeric biodegradable materials may also be present.

Biodegradation refers to hydrolytic, enzymatic and other metabolic breakdown processes in the living organism, which are caused primarily by the body fluids coming in contact with the endoprosthesis and result in a gradual dissolution of at least major parts of the scaffold or of the implant. A term that is frequently used synonymously with biodegradation is biocorrosion. The term bioresorption encompasses the subsequent resorption of the degradation products by the living organism. The objective of using biodegradable implants is to have these degraded by the organism at a point in time where they are no longer needed, for example with respect to the scaffolding action thereof, and therefore are present in the organism as foreign bodies no longer than is necessary.

Substances (base material) suitable for the scaffolds of biodegradable implants can be composed of one material or multiple materials. Examples of suitable polymer compounds include polymers from the group consisting of cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyorthoesters, polyethylene terephtalate (PET), polymalonic acid (PML), polyanhydrides, polyphosphazenes, polyamino acids and the copolymers thereof, as well as hyaluronic acid. Depending on the desired properties, the polymers may be present in pure form, in derivatized form, in the form of blends or as copolymers. Metallic biodegradable substances are based on magnesium, iron, zinc and/or tungsten alloys.

The position of a stent or other implants is frequently ascertained by imaging methods, such as by an X-ray irradiation device. Due to the small ordinal number and the low density of the biodegradable material, for example magnesium and the alloys thereof, the X-ray visibility of medical implants produced therefrom is very low. To eliminate this drawback, it is known to provide medical devices with marker elements that, at least in a portion of the volume thereof, comprises a material composition different from the material of the scaffold. These so-called (X-ray) markers or marker elements contain, in particular, a material that absorbs X-rays and/or other electromagnetic radiation to a greater degree (hereafter referred to as X-ray opaque or radiopaque material) than the material of the scaffold or the body environment of the patient, thereby becoming visible relative to the surrounding area thereof. Based on the ascertained position of the usually multiple marker elements on the scaffold, it is possible to determine the position and angular position of the implant with respect to the surrounding organs. When a biodegradable scaffold is used, a non-resorbable X-ray opaque or radiopaque material (such as Ta, Au, W) is frequently used for reasons of sufficient X-ray visibility.

Such a marker element is frequently cut off or out of a semi-finished product made of the material of the marker element and integrated into an implant in such a way that it is bonded into a corresponding opening (eyelet) provided for this purpose on the scaffold of the implant (for example, at both ends in the axial direction of the implant). Such marker elements and implants are known from the published, European patents or applications EP 2 399 619 B1 (corresponding to U.S. patent publication No. 2011/0319982), EP 3 165 238 A1 (corresponding to U.S. patent publication No. 2017/0119555) and EP 17 150 973.0 (unpublished as of yet), for example.

There is a technical requirement with regard to implants comprising integrated marker elements that the marker elements remain in the scaffold combination over a long period of time with a sufficiently high adhesive power. If the marker element is not sufficiently joined to the scaffold of the implant, an undesirable local element may form, or contact corrosion may be caused, as a result of metallic contact between the marker element and the scaffold material. This would result in premature detachment of the marker element from the scaffold of the implant, which would favor undesirable fragmentation and embolization. Moreover, it is to be prevented, in general, that the material of the marker element influences the degradation of the scaffold. With conventional bonding methods, additionally dosing of the adhesive is difficult since very small adhesive quantities are used for each marker element. It is also difficult the position the adhesive required for bonding, making this process often imprecise.

SUMMARY OF THE INVENTION

It is thus the object of the present invention to create an implant or a scaffold for an implant in which local element formation and corrosion are at least reduced. Accordingly, a marker element was to be created, which does not form a local element and avoids corrosion after integration into the implant. Moreover, cost-effective, simple and automatable methods for producing such a marker element, a scaffold comprising such an integrated marker element or an implant comprising such a scaffold are to be provided. In particular, the handling of the adhesive is to be improved.

The object is achieved by the method for producing a marker element described in the independent method claim.

The object is achieved, in particular, by a method for producing a marker element for an implant made of a layered or wire-shaped semi-finished product, comprising an X-ray opaque or a radiopaque material, wherein a respective adhesive layer is attached to or on at least one side of the semi-finished product, or a plurality of sections of the semi-finished product, so that a layer composite is formed at least in sections, and wherein subsequently a plurality of marker elements are cut out of the layer composite, or are detached from the layer composite, by appropriately cutting or appropriately severing (such as breaking away a web) in a direction transversely, and preferably perpendicularly, to the layers of the layer composite. The adhesive layer can be attached to the semi-finished product by use of coating (e.g. dip coating or spray coating), for example. It is possible for one or more further layers comprising an X-ray opaque or a radiopaque material to be provided in the layer composite.

The method according to the invention has the advantage that dosing of the adhesive for individual marker elements is eliminated. Marker elements that already comprise an adhesive layer which is exactly metered for the particular application and ideally positioned can be produced effectively by means of an automated method.

As an alternative, the individual marker elements can be coated as bulk material.

The resultant marker element can then be inserted into an opening (eyelet) of the scaffold and bonded thereto. If necessary, further treatments and/or coatings of the layer composite are carried out prior to detaching the marker element from the layer composite (see below).

The layered semi-finished product is formed, for example, by a film, a plate, a hollow cylinder (tube) or a three-sided, four-sided or more than four-sided, preferably straight, hollow prism, which is open at the two ends in the direction of a longitudinal axis.

The semi-finished product comprises an X-ray opaque or a radiopaque material in the form of a metal or a metal alloy, containing at least one metal or noble metal selected from the group consisting of the elements gold, platinum, tungsten, tantalum and titanium, or consists of such a metal or such a metal alloy. The semi-finished product is particularly preferably made of tantalum or a tantalum alloy. The described materials of the marker element have good X-ray absorption properties and can be provided, on the surface thereof, very easily with a dense, passivating and insulating (i.e., electrically non-conducting) oxide layer, e.g. by plasmaelectrolytic oxidation or other passivation methods (such as the use of a passivating coating comprising a polymer or parylene when using gold as the radiopaque material). In this way, they allow a marker element having a minimal size to be configured. The semi-finished product is preferably produced by drawing from the respective material.

The detachment of the at least one section from the semi-finished product (for example after cleaning (pickling) and/or passivation treatment) takes place by cutting (e.g., by means of laser), breaking away a web or mechanical cutting from the semi-finished product. If necessary, the section can be detached from the semi-finished product along a portion of the contour, so that the section is still connected to the semi-finished product by at least one web. Afterwards, cleaning (pickling) and/or a passivation treatment can take place. Thereafter, the section is completely detached from the semi-finished product by means of severing (e.g., by use of laser or by use of a mechanical cutting tool).

The adhesive layer preferably comprises a thermoplastic elastomer (TPE) or consists of a TPE. TPEs (also referred to as elastoplasts on occasion) are plastic materials that behave similarly to the traditional elastomers at room temperature, but can be plastically deformed when heat is supplied and thus exhibit thermoplastic behavior. TPE encompasses the following material classes, for example:

a) PE-A or TPA (thermoplastic copolyamides, e.g. PEBAX (Arkema));

b) TPE-E or TPC (thermoplastic polyester elastomers/thermoplastic copolyesters, e.g. Keyflex (LG Chem));

c) TPE-O or TPO (olefin-based thermoplastic elastomers, primarily PP/EPDM);

d) TPE-S or TPS (styrene block copolymers (SBS, SEBS, SEPS, SEEPS and MBS), e.g. Kraton (Kraton Polymers), Septon (Kuraray), Styroflex (BASF), Thermolast (Kraiburg TPE) or Saxomer (PCW));

e) TPE-U or TPU (urethane-based thermoplastic elastomers, e.g. Elastollan (BASF) or Desmopan, Texin, Utechllan (Bayer)); and f) TPE-V or TPV (thermoplastic vulkanizates or cross-linked olefin-based thermoplastic elastomers, predominantly PP/EPDM, e.g. Sarlink (DSM)).

Elastic adhesives have the advantage that they contribute to improved trackability, i.e., to the adaptation to the surrounding tissue as the implant is advanced during insertion, whereby premature loss of a marker element is avoided.

For example, polyurethane dissolved in dimethylformamide can be used as a TPE adhesive. Alternative adhesives from the above material classes are likewise conceivable, preferably together with a suitable solvent, which evaporates under the action of heat so as to effect curing of the adhesive.

As an alternative or in addition, the adhesive layer can comprise a resin and/or shellac and/or a low viscosity adhesive.

In addition to polyurethane, a degradable polymer (e.g. PLLA L210, PLLA L214), for example, can be used as an advantageous polymer-based adhesive. These adhesives are particularly biocompatible and also provide good electrical insulation.

In a preferred exemplary embodiment, in the method for producing the marker element using a layered (i.e., film-like, plate-shaped or hollow body-shaped) semi-finished product a continuous first layer or a plurality of sections of a first layer of the semi-finished product is/are arranged on a first side of the adhesive layer, and a continuous second layer or a plurality of sections of a second layer of the semi-finished product is/are arranged on a second side of the adhesive layer located opposite the first side, and are attached thereto, whereby these form the layer composite at least in sections.

With the method described in this exemplary embodiment, a marker element having a sandwich design is created, which has the advantages described below when bonded into an opening of the scaffold.

The above exemplary embodiment of a method for producing a marker element can be automated well, in particular, when a continuous first layer of a film-like semi-finished product, comprising an X-ray opaque or a radiopaque material, is arranged on a first side of the adhesive layer, and a continuous second layer of a film-like semi-finished product, comprising an X-ray opaque or radiopaque material, is arranged on the second side of the adhesive layer located opposite the first side, and are attached thereto, whereby these form the layer composite at least in sections.

The above object is further achieved by a method for producing a scaffold, preferably made of a magnesium alloy, and in particular of a rare earth-containing magnesium alloy, a magnesium zinc aluminum alloy or a magnesium zinc calcium alloy, for an implant including a marker element, comprising a layer composite including at least one layer comprising an X-ray opaque or a radiopaque material and an adhesive layer. The marker element is introduced into an opening of the scaffold and, using a heat source, the marker element is heated in such a way that the adhesive layer of the marker element becomes softened or liquefied, so that the adhesive of the adhesive layer creates an adhesive joint with the inner surface of the opening.

In the method according to the invention, the marker element preferably has a composition different from the material of the scaffold.

According to the invention, the at least one marker element is attached to the scaffold by means of an adhesive, and preferably by means of an adhesive comprising or consisting of TPE. This is because it was found that, in particular, an integral joint achieves a simple and mechanical joint that does not strain the filigree scaffold. In addition, by adapting the shape of the marker element to the shape of the opening (eyelet, receptacle) on the scaffold of the implant into which the marker is introduced, or conversely, a form fit can be achieved. However, the inside dimensions (e.g. the inner width and length) of the opening are slightly larger than the outside dimensions of the marker element, whereby a gap still remains between the marker element and the inner edge of the opening around the outer edge of the marker element after having introduction into the opening, the adhesive being able to flow into this gap after softening or liquefying so as to establish an integral joint between the marker element and the opening.

In one exemplary embodiment, the opening is configured as a through-opening.

In one refinement of the invention, using a marker element comprising a layer composite including at least one first layer and one second layer, each comprising an X-ray opaque or a radiopaque material, and an interposed adhesive layer, the marker element, after having been introduced into an opening of the scaffold, is subjected to a pressure force in a direction transversely to the layers of the layer composite, and preferably perpendicularly to the layers of the layer composite, in such a way that the adhesive exits on the lateral face of the marker element and creates an adhesive joint with the inner surface of the opening. The pressure force can be applied, for example, by means of appropriate crimping pliers or an appropriate crimping tool and causes the adhesive to be distributed in the gap between the marker element and the inner edge of the opening. Compressing the first layer and the second layer comprising the X-ray opaque or radiopaque material reduces the space available for the adhesive between these layers, causing the adhesive to ooze out on the side of the marker element into the adhesive gap between the marker element and the opening. In the case of a hollow cylindrical scaffold, the pressure force preferably extends in the radial direction. This exemplary embodiment is particularly well-suited for further automation of the method and achieves particularly good results with respect to the bond to the scaffold and the avoidance of the formation of local elements. Advantageously, no capillary action is required with this exemplary embodiment to distribute the adhesive in the adhesive gap.

In a preferred exemplary embodiment, the scaffold is placed on a mandrel, which fills the inner volume of the scaffold, before the marker element is introduced into the opening. In the case of a hollow cylindrical scaffold, the mandrel can have the shape of a cylinder, for example. The mandrel forms an abutment for applying the pressure force and can be removed again after the at least one marker element has been attached by bonding.

In a further exemplary embodiment, the marker element is heated by the heat source, before or after the pressure force is applied to the marker element, in such a way that the adhesive layer of the marker element is softened or liquefied. In this exemplary embodiment, the lateral exiting (oozing) of the adhesive out of the sandwich layer composite is particularly favored.

In a further exemplary embodiment, the scaffold is provided, at least in a predefined area, with a coating containing a pharmaceutically active substance before the marker element is bonded in.

A "pharmaceutically active substance" (or therapeutically active or effective substance) shall be understood to mean a plant, animal or synthetic active ingredient (drug) or a hormone, which is used in a suitable dose as a therapeutic agent for influencing states or functions of the body, for substituting active ingredients produced naturally by humans or the animal body, such as insulin, and for eliminating or rendering harmless pathogens, tumors, cancer cells or substances foreign to the body. An antiproliferative active ingredient, such as paclitaxel, sirolimus or everolimus, is preferably used as the pharmaceutically active substance.

As an alternative or in addition, the scaffold is provided, at least in a predefined area, with a coating containing a pharmaceutically active substance after the at least one marker element has been bonded in.

The above object is further achieved by a disk-shaped marker element for an implant comprising a layer composite including at least one first layer comprising an X-ray opaque or a radiopaque material and an adhesive layer that is joined to the first layer and arranged so as to adjoin the first layer. The first layer and the adhesive layer are separated from the semi-finished product by means of a cut extending through the first layer and the adhesive layer.

By arranging the adhesive layer on the X-ray opaque or radiopaque first layer and cutting the layer composite as a whole out of these layers of the semi-finished product, dosing and positioning of the adhesive before the marker element is bonded into the scaffold or the opening thereof are eliminated.

The disk-shaped marker element is preferably made of tantalum, tungsten, gold, platinum or another material having similarly high radiodensity.

The above object is further achieved by a scaffold for an implant comprising an above-described marker element, wherein the marker element is bonded into an opening (eyelet) of the scaffold. The bonding method was already described above in detail.

The above object is also achieved by an implant comprising an above-described scaffold with the same advantages.

The invention will be described hereafter based on exemplary embodiments and with reference to the figures. All described and/or illustrated features, either alone or in any arbitrary combination, form the subject matter of the invention, independently of their combination in the claims or their dependency references.

Other features which are considered as characteristic for the invention are set forth in the appended claims.

Although the invention is illustrated and described herein as embodied in a marker element and a method for the production thereof, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIGS. 3A-3E are illustrations of a first exemplary embodiment of a method according to the invention for producing a marker element in a respective sectional view (FIGS. 3A-3C) and the marker element produced thereby in a view from the side (FIG. 3D) and in a perspective view from the side (FIG. 3E);

FIGS. 8A-8D are sectional views showing an exemplary embodiment of a method according to the invention for producing a scaffold for an implant in individual steps;

FIGS. 10A-10C show an exemplary embodiment of a method according to the invention for producing a scaffold for an implant comprising a marker element according to FIG. 7 in individual steps, each in a sectional illustration;

DETAILED DESCRIPTION OF THE INVENTION

Figure 1:
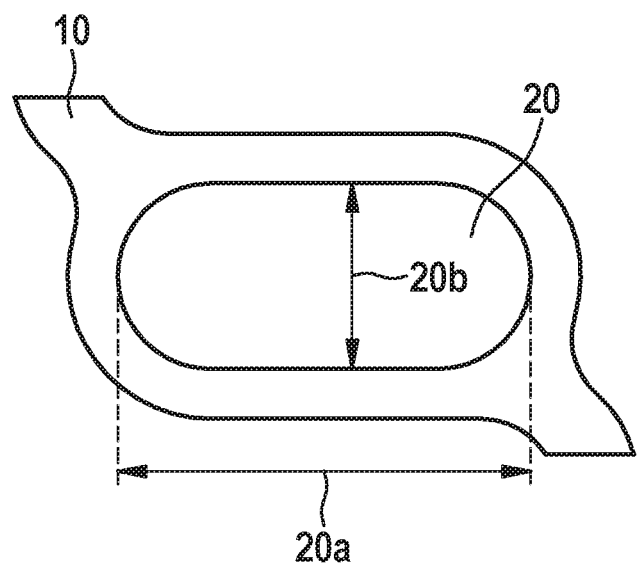
FIG. 1 is a top plan view of a section of a scaffold of an implant.

FIG. 1 shows a section of a scaffold 10 of an implant according to the invention in the form of a medical stent, for example made of the degradable magnesium alloy WE43. FIG. 1 shows a through-opening (hereafter eyelet) 20 having an elliptic basic shape, which is provided at the distal or proximal end of the scaffold 10, for example. At the distal and/or at the proximal end of the scaffold 10 of the implant, a respective eyelet 20 is, or three eyelets 20 offset by 120° are, provided as components of the scaffold, for example on a strut. The scaffold is preferably formed as a hollow cylindrical mesh comprising a plurality of struts. For example, the dimensions of the eyelets 20 are 800 µm (dimension 20a in FIG. 1)×350 µm (dimension 20b in FIG. 1).

Figure 2:
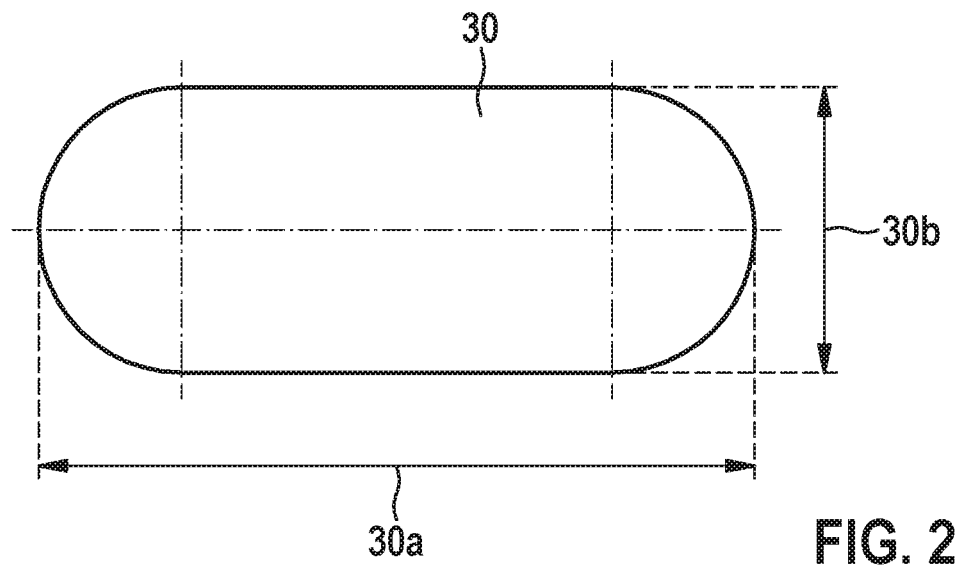
FIG. 2 shows a marker element in a view from above.

An X-ray opaque marker element 30 (see FIG. 2), which, as is described hereafter, can be attached to the eyelet 20 by means of an adhesive layer, can be arranged in the eyelet 20.

The X-ray opaque material used in the marker element 30 can be predominantly made of tantalum (e.g. having a purity of 99.9%) or a tantalum alloy. The thickness of the marker element 30 is 100 µm, for example. The wall thickness of the scaffold 10 can be 100 µm, for example. The dimensions of the marker are, for example, 750 µm (dimension 30a in FIG. 2)×300 µm (dimension 30b in FIG. 2).

In the first exemplary embodiment shown in FIG. 3 for producing a marker element 30, initially a semi-finished product in the form of a film-like first layer 31 made of the X-ray opaque or radiopaque material, for example tantalum (e.g. having a purity of 99.9%) or a tantalum alloy, is provided with an adhesive coating 33, made of a TPE for example. The adhesive coating is made of polyurethane dissolved in dimethylformamide, for example, and has a thickness of approximately 0.025 mm. On the side located opposite the first layer 31, a second layer 32 made of the X-ray opaque or radiopaque material, for example tantalum or a tantalum alloy, is then applied to the adhesive coating 33. The resultant layer composite is shown in FIG. 3A.

In the second step, individual marker elements 30 are now cut out of the layer composite by means of a cutting method, for example by means of laser cutting or another mechanical cutting method. The cutting is illustrated in FIG. 3B by dotted lines 34. The cut extends perpendicularly to the layers 31, 32, 33 of the layer composite. The marker elements 30 thus separated each comprise a layer composite including three layers, wherein the adhesive layer 33 is arranged in a sandwich-like manner between the first layer 31 and the second layer 32 comprising the X-ray opaque or radiopaque material. This is also apparent in FIGS. 3D and 3E, which each show an individual marker element 30.

Figure 4A:
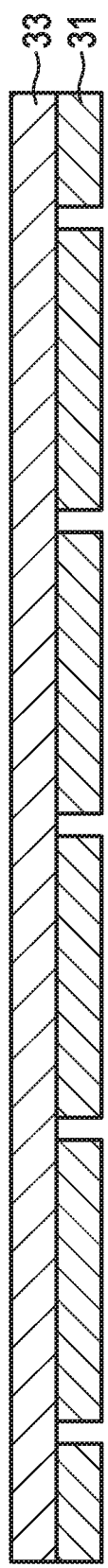
FIGS. 4A-4D show a second exemplary embodiment of a method according to the invention for producing a marker element in a respective sectional view (FIGS. 4A-4B) and the marker element produced thereby in a view from the side (FIG. 4C) and a perspective view from the side (FIG. 4D)
Figure 4B:
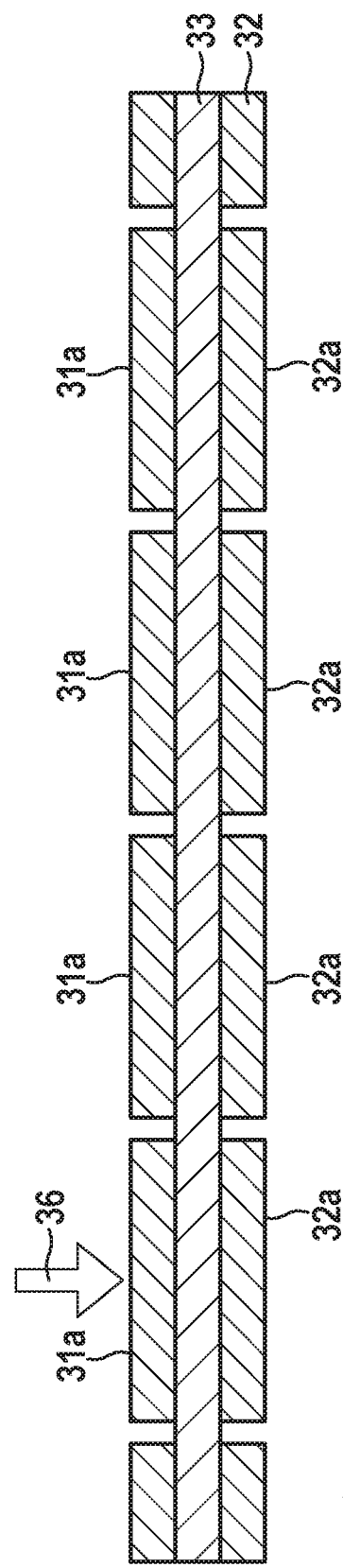
Figure 4D:
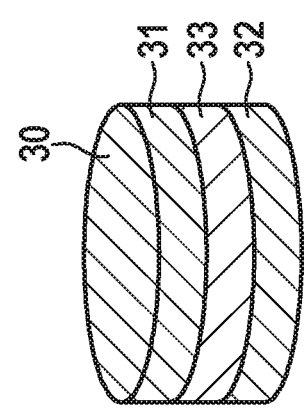
Figure 4C:
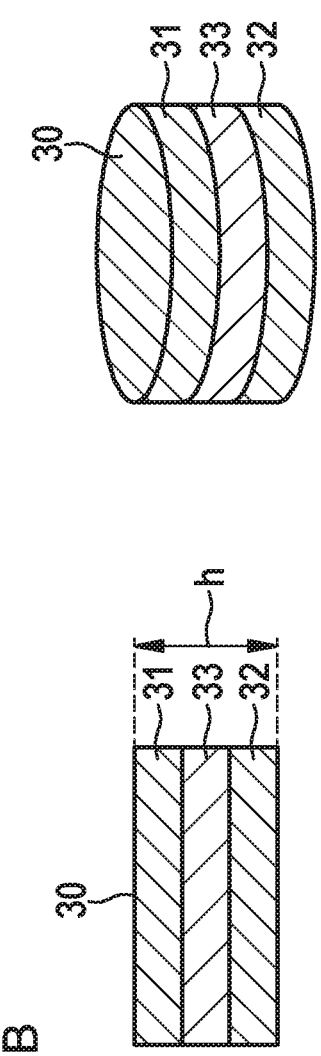

As an alternative, a semi-finished product in the form of a film-like first layer 31 comprising an X-ray opaque or a radiopaque material, including partially cut-out sections 31a for the marker element, can be provided on one side with an adhesive layer 33 (for example, made of a TPE) (see FIG. 4A). Afterwards, a further semi-finished product in the form of a film-like second layer 32 comprising an X-ray opaque or a radiopaque material, including partially cut-out sections 32a, is applied to the second side of the adhesive layer 33 located opposite the first layer 31 (see FIG. 4B). The surfaces of the layers 31a and 32a can have been passivated before the adhesive coating is applied. Such passivation can take place, for example, by means of plasmaelectrolytic treatment (plasmaelectrolytic oxidation). The respective sections 31a, 32a are located on top of one another. Here, "partially cut-out" shall be understood to mean that the respective section 31a, 32a is still connected to the remaining material of the respective layer 31, 32 by at least one web (not shown). Afterwards, as is shown in FIG. 4B, the marker element is separated (pushed out) by means of a force in a direction perpendicular to the layers 31, 32, 33 (see arrow 36) by severing the at least one web of the sections 31a, 32a. The interposed adhesive layer 33 is likewise severed. The separation can also take place by means of laser cutting or another mechanical cutting method. The individual marker element 30, which is shown in FIGS. 4C and 4D, has the same composition as a marker element 30 produced according to FIGS. 3A-3D.

Figure 5:
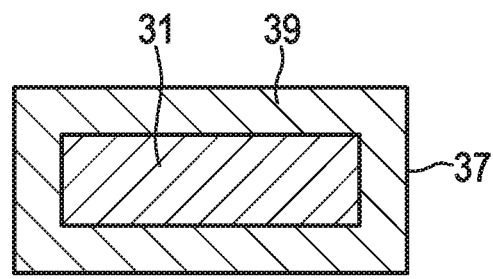
FIG. 5 is a diagrammatic, a cross-sectional view of a second exemplary embodiment of a marker element.

FIG. 5 shows a marker element 37 comprising a plate-shaped first layer 31 made of an X-ray opaque or a radiopaque material, for example tantalum or a tantalum alloy, which in an already cut (separated) state was provided on the entire surface thereof with an adhesive layer 39. Such a coating can be implemented, for example, by means of dipping in an appropriate solution or by means of spraying as bulk material consisting of a plurality of plate-shaped first layers 31.

Figure 6:
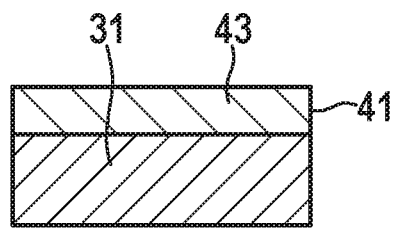
FIG. 6 is a side view of a third exemplary embodiment of a marker element.
Figure 7A:
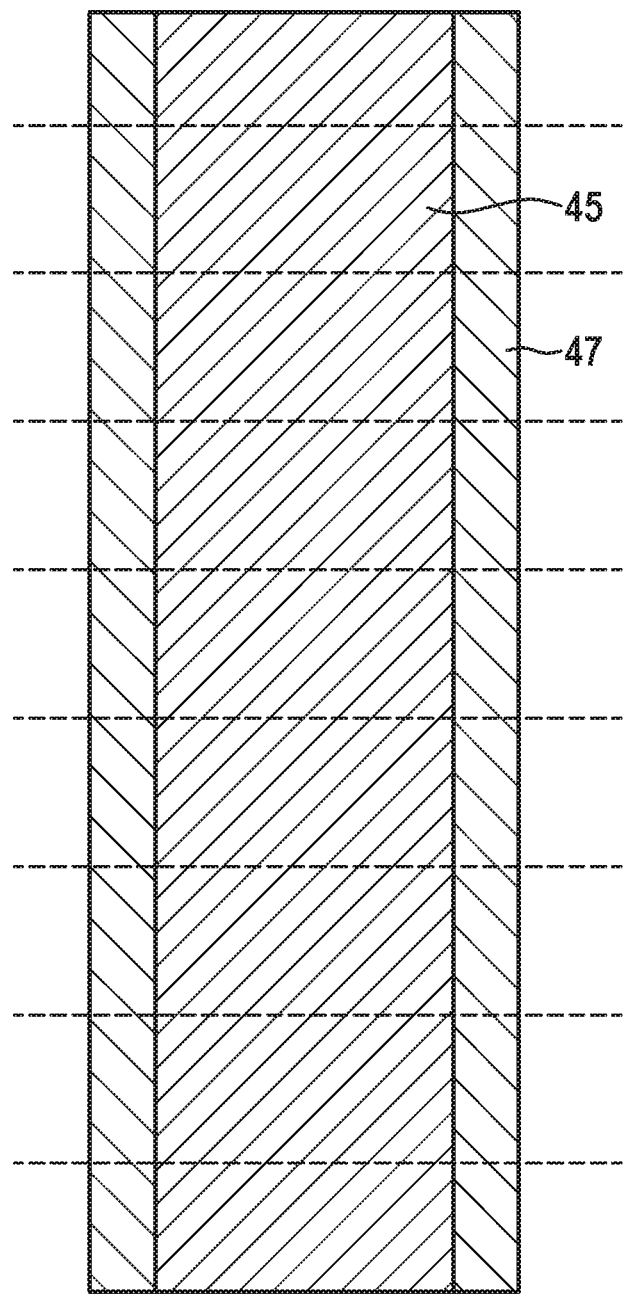
FIGS. 7A-7D show a third exemplary embodiment of a method according to the invention for producing a marker element (FIG. 7A) and the marker element produced thereby in a cross-sectional view (FIG. 7B), a view from above (FIG. 7C) and a perspective view from the side (FIG. 7D)
Figure 7B:
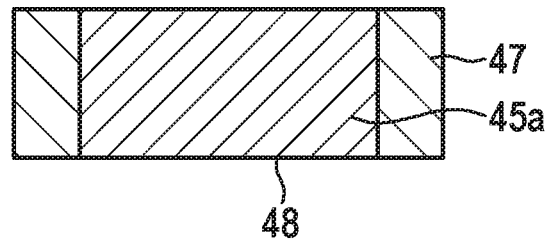
Figure 7C:
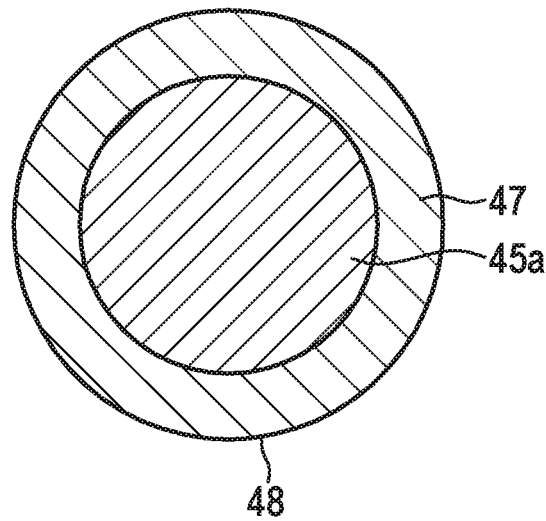
Figure 7D:
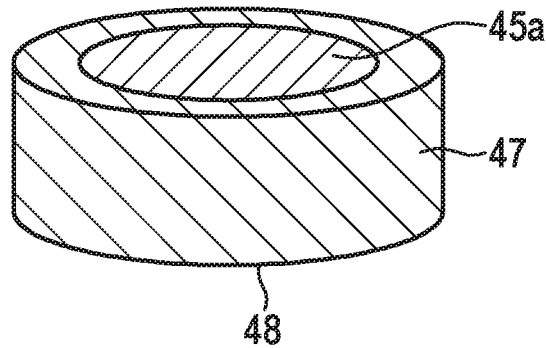

FIG. 6 shows a marker element 41 comprising a plate-shaped first layer 31 made of an X-ray opaque or a radiopaque material, for example tantalum or a tantalum alloy, which on a portion of the surface thereof was provided with an adhesive coating 43.

FIG. 7 shows a method for producing a marker element in which a cylindrical wire 45 made of the X-ray opaque or radiopaque material, for example tantalum or a tantalum alloy, was initially provided on the lateral surface thereof with an adhesive layer 47, and in particular a TPE material. The surface of the wire 45 can have been passivated before the adhesive coating 47 is applied.

Afterwards, the wire is cut in a direction transversely (e.g. perpendicularly) to the longitudinal axis thereof so as to form individual marker elements 48. The progression of the cuts is illustrated with dotted lines 49 in FIG. 7A. The cutting can take place by means of laser cutting or other known cutting methods, for example. The resultant marker elements 48 are shown in different views in FIGS. 7B to 7D. The marker elements 48 are characterized by comprising a small cylindrical plate 45a, which on the circumference thereof is provided with the adhesive coating 47 (see FIGS. 7B to 7D).

Based on FIGS. 8A-8D, it will now be described how a marker element 30 produced according to FIGS. 3A-4D or is introduced into an opening (eyelet) 20 of a scaffold 10 and joined thereto.

Before the marker element 30 is placed into the eyelet 20, the scaffold 10 which is to be provided with at least one marker element is threaded onto a mandrel 50. This means that the substantially hollow cylindrical scaffold 10 is placed on a cylindrical mandrel 50 in such a way that the mandrel 50 takes up the entire inside volume of the hollow cylindrical scaffold 10, and that the lateral surface of the mandrel 50 rests directly against the inside of the struts of the scaffold 10.

After the scaffold 10 has been placed on the mandrel 50, the marker element 30 is now inserted into an appropriate eyelet 20 (see FIG. 8A). It is apparent from the figure that an adhesive gap 21 is formed between the lateral surface of the marker element 30 and the inner edge of the opening 20 in that the outside dimensions of the marker elements 30 are slightly smaller than the inside dimensions of the opening 20. Afterwards, the marker element 30 is heated under the action of an appropriate heat source 53, whereby the adhesive layer 33 is softened. This is shown in FIG. 8B. FIG. 8C illustrates that, in the following step, the marker element 30 protruding slightly in height h beyond the eyelet 20 is pressed together, for example by means of a crimping tool 60 shown in FIG. 9. The direction of the compression force is a direction transversely (e.g. perpendicularly) to the progression of the layers or of the longitudinal axis of the scaffold 10. The direction of the force is illustrated in FIG. 8C by an arrow 55.

The introduction of the mechanical force causes the two layers 31, 32 of the marker element 30 to be compressed, whereby the available volume is reduced for the softened adhesive of the adhesive layer. Consequently, the softened adhesive 33a from the adhesive layer 33 is pushed out of the side of the marker element 30, so that the adhesive flows into the empty volume of the adhesive gap 21 between the marker element 30 and the inner edge of the eyelet 20 of the scaffold 30 and bonds to the inner edge of the eyelet 20. In this way, good joining between the marker element 30 and the scaffold 10 by means of adhesive can be achieved using a method that can be carried out automatically. The adhesive 33a completely fills the adhesive gap 21. This state is shown in FIG. 8D.

Figure 9:
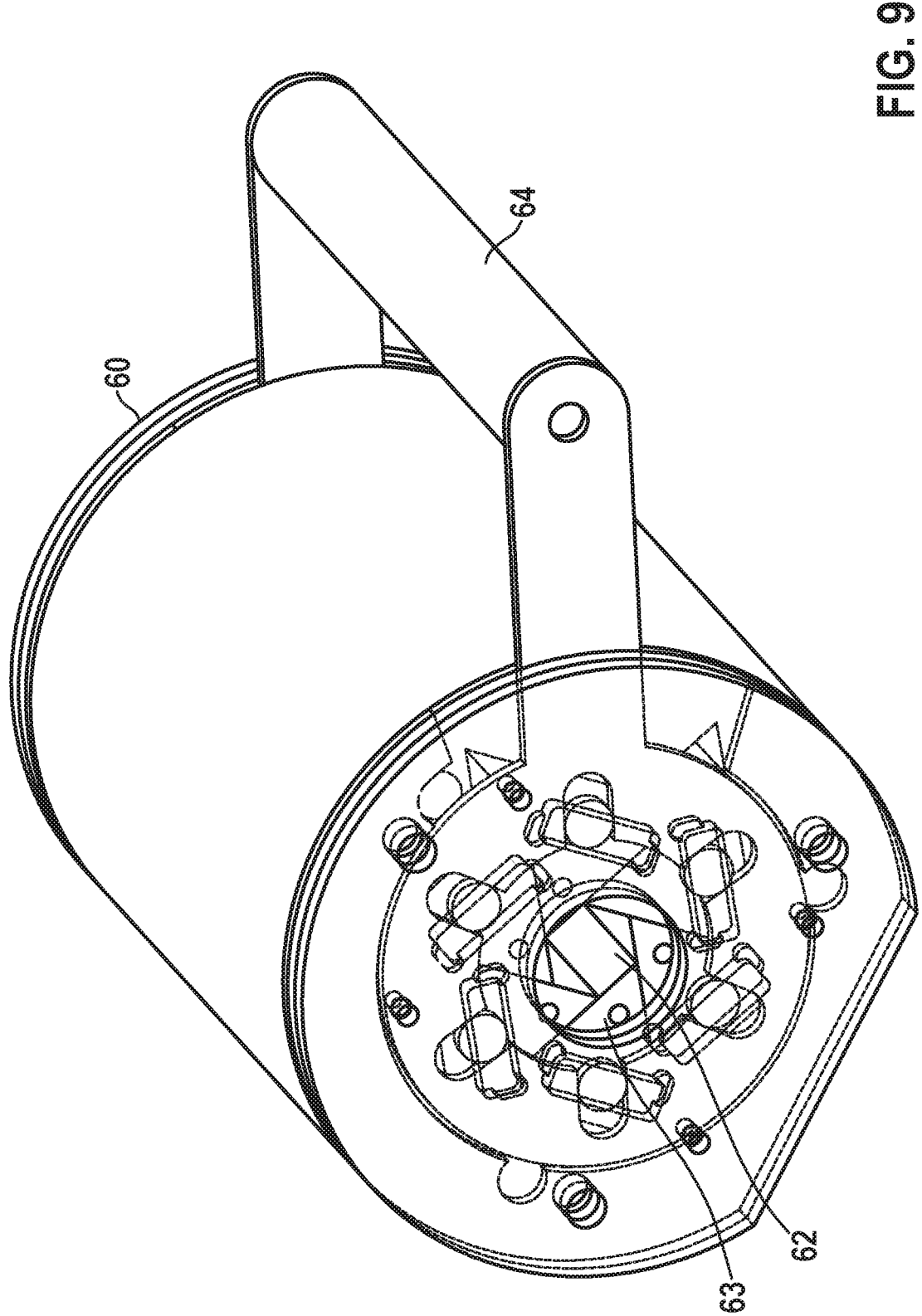
FIG. 9 is a side, perspective view of a tool for producing the scaffold.
Figure 11A:
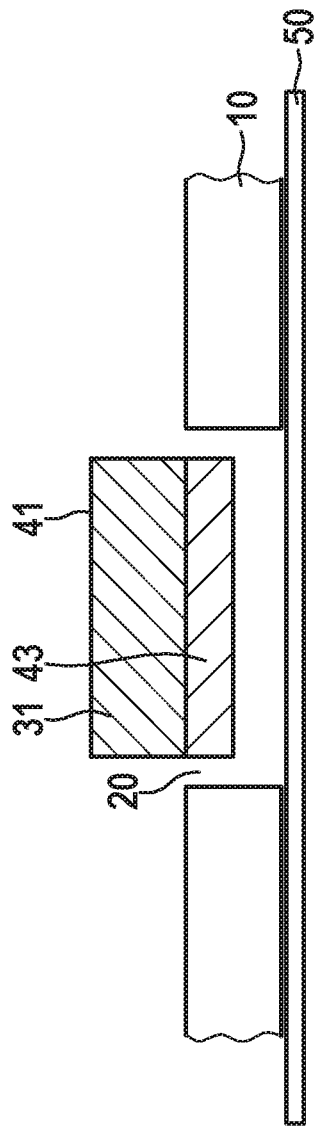
FIGS. 11A-11D show an exemplary embodiment of a method according to the invention for producing a scaffold for an implant comprising a marker element according to FIG. 6 in individual steps, each in a sectional illustration.
Figure 11B:
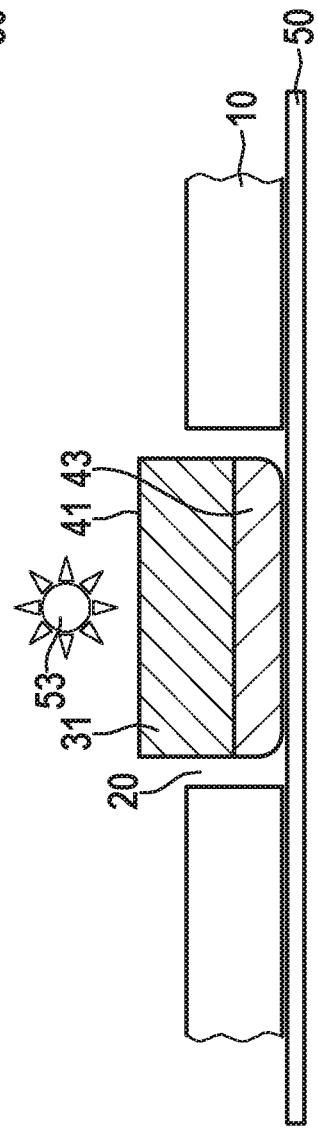
Figure 11C:
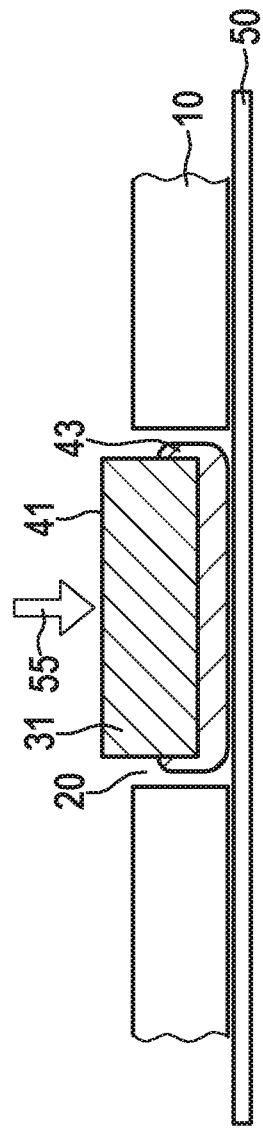
Figure 11D:
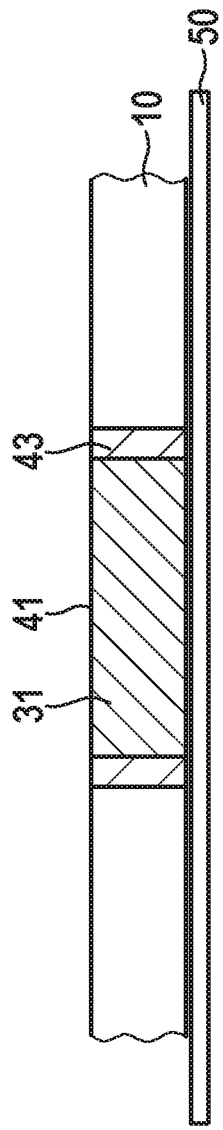
Figure 12A:
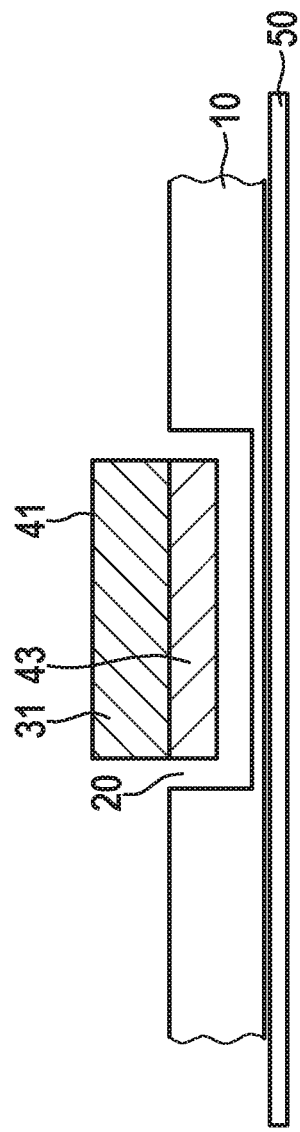
FIGS. 12A-12D show an exemplary embodiment analogous to FIGS. 11A-11D, wherein the opening for the marker element is designed as a pocket here.
Figure 12B:
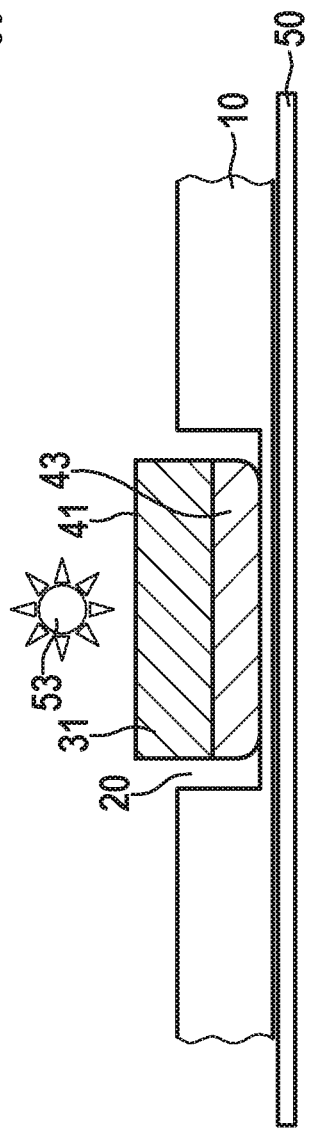
Figure 12C:
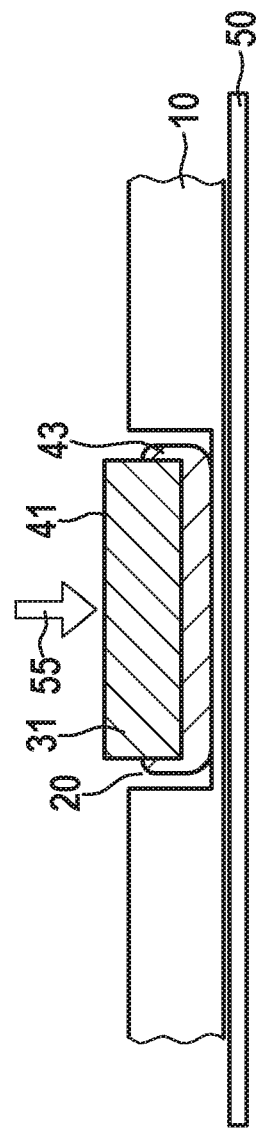
Figure 12D:
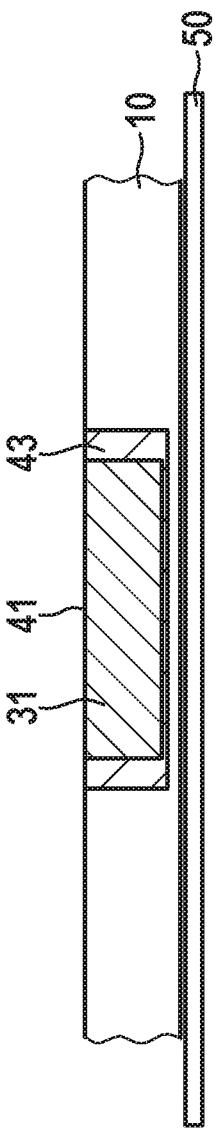

The crimping tool 60 shown in FIG. 9 has a cylindrical opening 62, into which the scaffold 10 threaded onto the mandrel 50 is introduced together with the marker element 30, which is not fully attached yet. A number of jaws 63 are arranged around the circumference of the opening 62, which when the handle 64 connected to the jaws 63 is pressed down are guided in such a way that the diameter of the opening 62 is decreased. In this way, the above-described force can be applied to the marker element 30 perpendicularly to the layers of the marker element 30 so as to laterally push out the adhesive 33a from the adhesive layer 33 to bond with the eyelet 20.

After the pressing in the crimping tool 60 and curing by cooling of the adhesive 33a, the scaffold 10 is removed from the crimping tool 60 again. Afterwards, the mandrel 50 can be removed from the scaffold 10 again.

Using a simple method that is simple to automate, a permanent joint can thus be created between the marker element 30 and the scaffold 10, in which the dosing of the adhesive and the application thereof can be achieved without difficulty and with precision.

The mounting of a marker 48 (FIGS. 10A-10C), in principle, does not differ from a marker 30. The adhesive is already present on the circumference of the marker. Since the adhesive is liquefied before the marker 48 is pressed in, it is possible to compensate for shape tolerances of the eyelet. Accordingly, a smaller adhesive gap is provided here than in the embodiment according to FIGS. 8A-8D. The heated adhesive automatically fills the gap between the marker 48 and the stent 10.

FIGS. 11A-12D show the mounting of a marker 41. This variant is advantageous in particular when the eyelet is not formed as a through-opening, but as a pocket (see FIGS. 12A-12D).

In general, identical components are denoted by identical reference numerals within the scope of the drawings.

The invention claimed is:

1. A method for producing a marker element for an implant, which comprises the steps of:
provuding a layered semi-finished product or a plurality of sections of a layered semi-finished product formed by a film or by a plate from an X-ray opaque or a radiopaque material;
attaching a respective adhesive layer onto at least one side of the layered semi-finished product or the plurality of sections of the layered semi-finished product that are disposed next to one another so that a layer composite is formed in the form of a film or plate or in a plurality of sections; and subsequently cutting a plurality of marker elements out of the layer composite, or detaching from the layer composite, by cutting or severing in a direction transversely to layers of the layer composite;

wherein:
the layered semi-finished product is a layered semi-finished product formed from the X-ray opaque or the radiopaque material and having a first layer which is a continuous first layer or a sectioned first layer having a plurality of sections, the first layer disposed on a first side of the respective adhesive layer; and the layered semi-finished product having a second layer is a continuous second layer or a sectioned second layer with a plurality of sections, the second layer being disposed on a second side of the respective adhesive layer located opposite the first side, and attached thereto, whereby the first and second layers with the respective adhesive layer form said layer composite at least in sections.

2. The method according to claim 1, wherein the respective adhesive layer comprises a thermoplastic elastomer.

3. The method according to claim 1, wherein the cutting or the severing is performed in a direction transversely and perpendicularly to the layers of the layer composite.

4. A method for producing a scaffold for an implant, which comprises the steps of:

providing a marker element containing a layer composite formed in the form of a film or plate or in a plurality of sections, the layer composite being formed of at least one layer having an X-ray opaque or radiopaque material and an adhesive layer, said at least one layer formed by a film or by a plate;

introducing the marker element into an opening of the scaffold;

heating the marker element in such a way that the adhesive layer of the marker element becomes softened or liquefied, so that an adhesive of the adhesive layer creates an adhesive joint with an inner surface of the scaffold defining the opening; and wherein:
the layer composite has a first layer that is a continuous first layer or a sectioned first layer having a plurality of sections, the first layer disposed on a first side of a respective adhesive layer; and the layer composite has a second layer that is a continuous second layer or a sectioned second layer with a plurality of sections, the second layer being disposed on a second side of a respective adhesive layer located opposite the first side, and attached thereto, whereby the first and second layers with the respective adhesive layer form said layer composite or in a plurality of sections.

5. The method according to claim 4, wherein, the first layer and the second layer are formed to each have the X-ray opaque or radiopaque material, and wherein the method further comprises the step of:

subjecting the marker element, after having been introduced into the opening of the scaffold, to a pressure force in a direction transversely to the first and second layers of the layer composite in such a way that the adhesive exits on a lateral face of the marker element and creates the adhesive joint with the inner surface of the scaffold defining the opening.

6. The method according to claim 5, which further comprises heating the marker element before or after the pressure force is applied to the marker element, in such a way that the adhesive layer of the marker element is softened or liquefied.

7. The method according to claim 4, which further comprises providing the scaffold, at least in a predefined area, with a coating having a pharmaceutically active substance before the marker element is bonded into the opening of the scaffold.

8. The method according to claim 4, which further comprises providing the scaffold, at least in a predefined area, with a coating having a pharmaceutically active substance after the marker element has been bonded into the opening of the scaffold.

9. A disk-shaped marker element for an implant, the disk-shaped marker element comprising:

a layer composite formed in a form of a film or plate, and including at least one first layer having an X-ray opaque or radiopaque material and an adhesive layer, said at least one first layer including:

a first layer that is a continuous first layer or a sectioned first layer having a plurality of sections, said first layer formed by a film or by a plate and disposed on a first side of said adhesive layer; and a second layer that is a continuous second layer or a sectioned second layer with a plurality of sections, said second layer formed by a film or by a plate and disposed on a second side of said adhesive layer located opposite the first side, and attached thereto, whereby the first and second layers with the respective adhesive layer form said layer composite at least in sections.

10. The marker element according to claim 9, wherein said first layer and said second layer are formed of the X-ray opaque or radiopaque material.

11. A scaffold for an implant, the scaffold comprising:
a scaffold body having an opening formed therein; and
a disk-shaped marker element according to claim 9, said disk-shaped marker element being bonded into said opening of said scaffold body.

12. An implant, comprising:
a scaffold having an opening formed therein, said scaffold containing a disk-shaped marker element according to claim 9 and an adhesive layer, said disk-shaped marker element being bonded into said opening of said scaffold.

* * * * *